(12) United States Patent
Bosoni

(10) Patent No.: US 10,168,045 B2
(45) Date of Patent: Jan. 1, 2019

(54) CANDLE POT

(71) Applicant: Maria Bosoni, Paris (FR)

(72) Inventor: Maria Bosoni, Paris (FR)

( * ) Notice: Subject to any disclaimer, the term of this patent is extended or adjusted under 35 U.S.C. 154(b) by 492 days.

(21) Appl. No.: 14/885,090

(22) Filed: Oct. 16, 2015

(65) Prior Publication Data

US 2017/0067629 A1    Mar. 9, 2017

(30) Foreign Application Priority Data

Sep. 8, 2015  (FR) ..................... 15 58349

(51) Int. Cl.
    *F23Q 13/00*   (2006.01)
    *F21V 35/00*   (2006.01)
    *A61L 9/00*    (2006.01)

(52) U.S. Cl.
    CPC .............. *F21V 35/003* (2013.01); *A61L 9/00* (2013.01); *F21V 35/00* (2013.01)

(58) Field of Classification Search
    CPC ........ F21V 35/003; F21V 35/00; F21V 23/04; F21V 33/0056; F21V 17/00; F21V 23/0407; F21V 23/0414; F21V 23/0435; F21V 29/20; F21V 29/74; F21V 33/0028; F21V 3/02; F21V 17/002; F21V 19/02; F21V 21/0824; A61L 9/00; F23D 3/08; F23D 14/52; F23D 3/16; F23D 3/18; F23D 3/24; A47G 19/2288; A47G 19/027; A47G 19/2272; A47G 2023/0283; A47G 23/0216; A47G 23/0306; A47J 39/025; A47J 27/21041
    See application file for complete search history.

(56) References Cited

U.S. PATENT DOCUMENTS

| | | | |
|---|---|---|---|
| 2002/0048739 A1* | 4/2002 | Chu | F21V 35/00 431/291 |
| 2014/0065278 A1* | 3/2014 | Feriola | A47J 37/01 426/523 |

\* cited by examiner

*Primary Examiner* — Jason Lau
(74) *Attorney, Agent, or Firm* — Bachman & LaPointe, P.C.

(57) ABSTRACT

A pot comprising a base and a peripheral wall defining a recess together wherein at least one lower portion of a combustible body is intended to be arranged to form a candle, the base comprising a network of elements extending in a relief pattern from the bottom face of said base, said network being arranged to be able to limit the thermal heating of said pot during the combustion of the body.

12 Claims, 2 Drawing Sheets

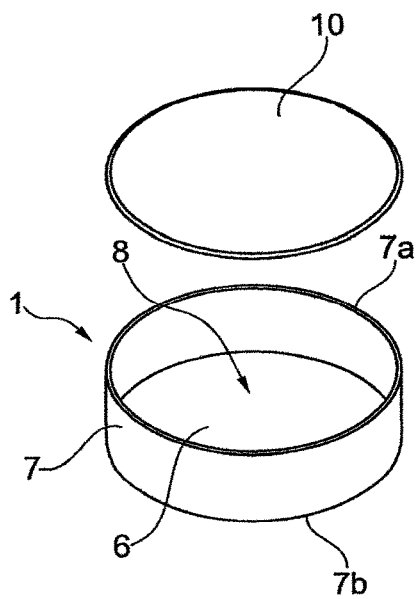
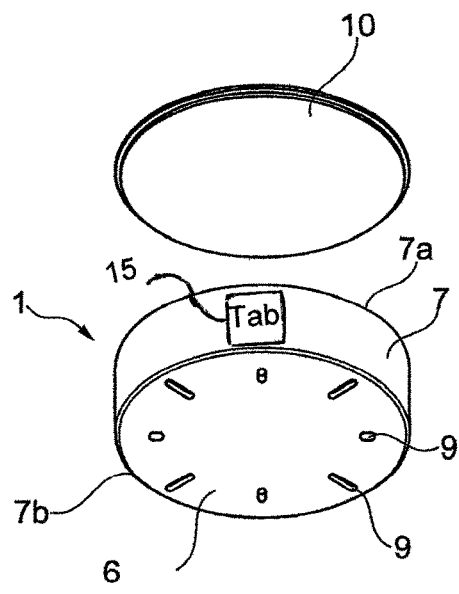
Fig. 1a
Fig. 1b
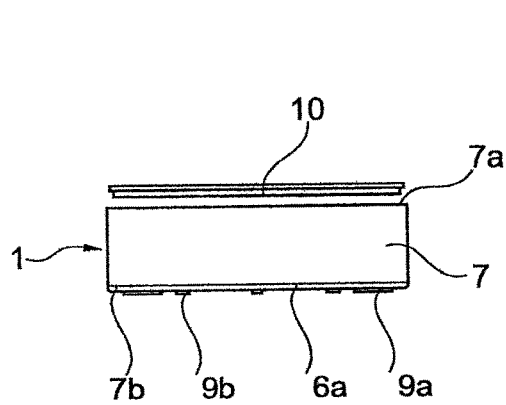
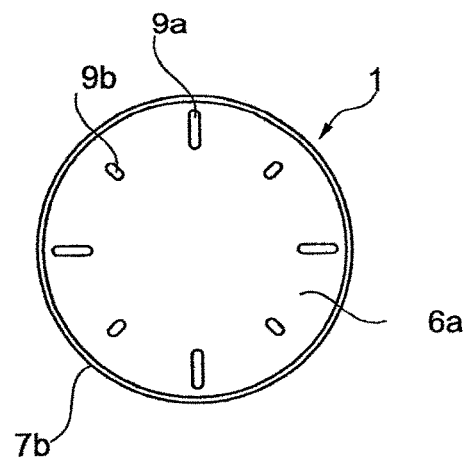
Fig. 2
Fig. 3

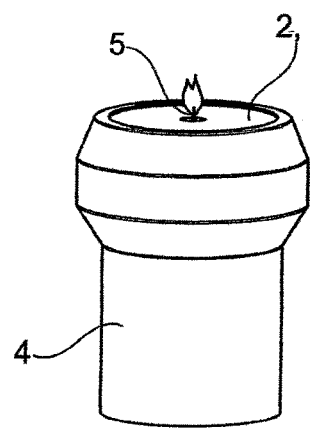
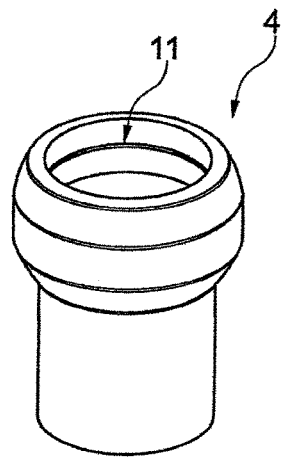
Fig. 4a                Fig. 4b
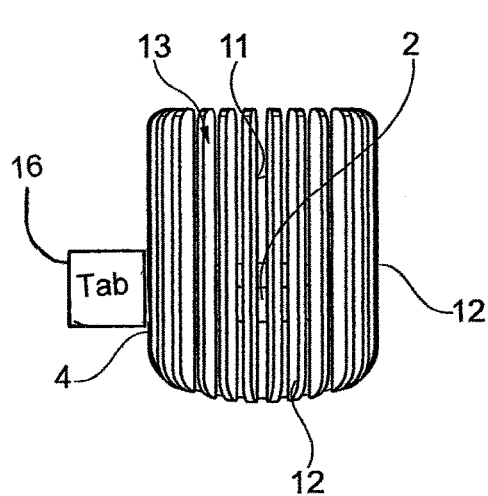
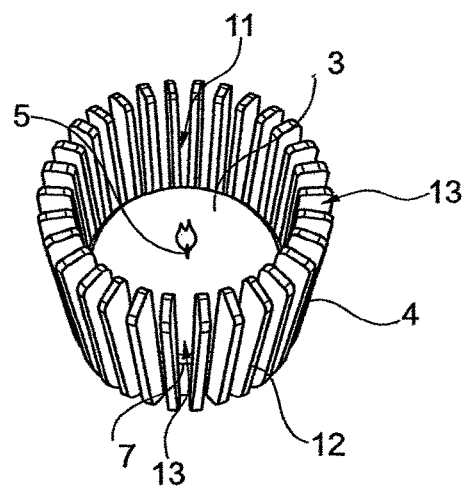
Fig. 5a                Fig. 5b

CANDLE POT

BACKGROUND

The invention relates to a pot comprising a base and a peripheral wall defining a recess together wherein at least one lower portion of a combustible body is intended to be arranged to form a candle, a candle comprising a body made of combustible material and such a pot, and an assembly comprising such a candle and a holder for receiving said candle.

It particularly applies to a candle wherein the pot and the combustible body have complementary peripheral geometries, said combustible body being arranged entirely in the recess of said pot.

In a known manner, this type of candle may be used alone or with a holder, for example a candle jar, a perfume burner, a candlestick or a plate warmer, notably for decorative purposes and/or for heating an aromatic, scented and/or food product.

As a general rule, the pot of such a candle is manufactured from a metallic material, for example aluminium, notably in order to simplify the production thereof and limit the costs thereof.

However, the use of such a material may pose a problem, notably due to the significant thermal conduction of said material. Indeed, during the use of the candle, the pot is subject to heating which increases as the body combusts, notably at the base thereof, which may cause damage on the surface whereon said base is arranged.

In addition, in the case whereby the combustible body is arranged entirely in the recess of the pot, the candle flame is continuously close to said pot, which increases the heating of said pot all the more, and thus the risks of damage to the supporting surface.

SUMMARY

The invention aims to improve the prior art by notably proposing a pot which is arranged to be able to limit the heating thereof during combustion of the body, notably so as to limit the risks of damage to the surface supporting the candle.

For this purpose, according to a first aspect, the invention relates to a pot comprising a base and a peripheral wall defining a recess together wherein at least one lower portion of a combustible body is intended to be arranged to form a candle, the base comprising a network of elements extending in a relief pattern from the bottom face of said base, said network being arranged to be able to limit the thermal heating of said pot during the combustion of the body.

According to a second aspect, the invention relates to a candle comprising a body made of combustible material and such a pot.

According to a third aspect, the invention relates to an assembly comprising such a candle and a holder for receiving said candle, said holder having a recess wherein at least the pot is intended to be arranged.

BRIEF DESCRIPTION OF THE DRAWINGS

Further specificities and advantages of the invention will emerge in the description hereinafter, with reference to the appended figures, wherein:

FIGS. 1a and 1b represent an exploded perspective view of a pot with a lid according to one embodiment of the invention, as a top view (FIG. 1a) and bottom view (FIG. 1b) respectively;

FIG. 2 represents a front view of the pot in FIG. 1, the lid being represented on top of said pot;

FIG. 3 represents a bottom view of the pot in FIGS. 1a, 1b and 2;

FIGS. 4a and 4 4b represent a holder for receiving a candle comprising a pot according to the invention, with a candle arranged in the recess (FIG. 4a) and alone (FIG. 4b) respectively;

FIGS. 5a and 5b represent an assembly according to one embodiment of the invention with the candle arranged in the recess of the holder, as a front view (FIG. 5a) and as a top perspective view (FIG. 5b) respectively.

DETAILED DESCRIPTION

With reference to these figures, a pot 1, a candle 2 comprising a body 3 made of combustible material and such a pot 1, as well as an assembly comprising such a candle 2 and a holder 4 for receiving said candle are described hereinafter.

The combustible material may be based on stearin and/or paraffin, or based on beeswax. Moreover, the combustible material may comprise at least one ingredient intended to enhance the visual appearance of the candle 2 and/or to produce an additional effect during the combustion of the body 3, for example a dye ingredient, an aromatic ingredient and/or a scented ingredient.

To enable combustion, a wick 5 made of inflammable material, for example consisting of a cotton yarn braid, is embedded in the combustible body 3 extending along the entire length of said body. Furthermore, the wick comprises a strand protruding out of the combustible body, in order to be able to light the candle 2 by igniting said strand.

With reference to FIGS. 1a, 1b, 2 and 3, the pot 1 comprises a base 6 and a peripheral wall 7, defining together a recess 8 wherein at least one lower portion of such a combustible body 3 is intended to be arranged to form a candle 2.

As a general rule, the peripheral wall 7 has a complementary geometry to that of the peripheral surface of the lower portion of the combustible body 3, so as to enable said peripheral wall to fit closely to said peripheral surface, and thus ensure satisfactory cohesion of the candle 2.

In the embodiment shown, the peripheral wall 7 has a cylindrical geometry. Alternatively, the peripheral wall 7 may have other types of geometries, for example oval or polygonal, according to the visual appearance sought for the candle 2.

In particular, as represented in FIGS. 4a and 5a and 5b, the combustible body 3 is arranged entirely in the recess 8 of the pot 1. The type of candle 2 thus formed makes it possible advantageously to prevent leakage of molten combustible material from the pot 1 during use of the candle, and thus limit the risks of burning and/or damage of the supporting surface whereon said candle is arranged.

Furthermore, this type of candle 2 proves to be relatively simple to manufacture, insofar as it is simply necessary to pour the molten combustible material of the body 3 into the recess 8, and allow said material to cool so as to form said combustible body in said recess by hardening said material.

In one particular application, the candle 2 is intended to become a scented cartridge, for example a luxury scented cartridge, notably having a circumference of more than 10 cm. In particular, each pot 1 containing the combustible body 3 forms a refill per se, intended to go into a holder 4, for example such as a candle jar, that has been specifically created.

The pot 1 may be manufactured using a metallic material, for example aluminium, notably in order to simplify the production thereof and limit the costs thereof. In particular, the pot 1 may be produced by cutting out a preform in an extra-thin aluminium sheet, notably of a few microns, and then by embossing said preform.

Furthermore, the top edge 7a of the peripheral wall 7, defining a top opening for access to the recess 8, may then undergo crimping, notably to limit the risks of cuts for the user.

However, the use of such a material may pose a problem, notably due to the high thermal conduction thereof. Indeed, during the use of the candle 2, the pot 1 is subject to heating which increases as the body 3 combusts, notably at the base 6 thereof, which may cause damage on the surface whereon said base is arranged.

In addition, in the case whereby the combustible body 3 is arranged entirely in the recess of the pot 1, the flame of the candle 2 is continuously close to said pot 1, which increases the heating of said pot all the more, and thus the risks of damage to the supporting surface.

To remedy these drawbacks, the base 6 of the pot 1 comprises a network of elements 9 extending in a relief pattern from the bottom face 6a of said base, said network being arranged to be able to limit the thermal heating of said pot during the combustion of the body 3.

The network may be produced when forming the pot 1, or during an additional step specifically relating to the base 6. In particular, the network may be produced by bossing or embossing the base 6.

When the pot 1 is placed on a supporting surface, only the elements in a relief pattern 9 come into contact with said surface, making it possible to form a passage for air circulation between the bottom face 6a and said supporting surface. As such, during the combustion of the body 3, the air circulation under the base 6 helps limit the thermal heating of the pot 1 by thermal convection.

Furthermore, due to the fact that the elements 9 protrude from the base 6, the network makes it possible to increase the total surface area of the bottom face 6a, and thus increase the thermal radiation at said bottom face, which also helps limit the heating of the pot 1.

Furthermore, the elements 9 of the network are distributed on the base 6 to provide support for the candle 2, notably in order to prevent any flow of molten combustible material via the top opening of the recess 8 when the candle 2 is placed on a supporting surface.

In the embodiment shown, the network comprises elements in a relief pattern 9 which are angularly equidistributed, notably with a constant angular distance in the region of 45°, on the bottom face 6a of the base 6.

In particular, the network comprises two types of elements in a relief pattern 9a, 9b of different geometries, said elements being angularly equidistributed according to a two-by-two alternation between said types. In the embodiment shown, the two types 9a, 9b of elements in a relief pattern have an oblong shape with identical widths, but different lengths, each element 9a, 9b being arranged along a radius of the bottom face 6a of the base 6.

As shown in FIGS. 1a, 1b and 2, the pot 1 comprises a lid 10 intended to be arranged reversibly on the top edge 7a of the peripheral wall 7 to seal the recess 8 by concealing the top opening thereof, notably for the purposes of visual appearance and/or to facilitate extinguishing the wick 5 at the end of the use of the candle 2.

Advantageously, the pot 1 may further comprise a gripping tab 15 extending radially from the peripheral wall 7, so as to facilitate handling of the candle 2 by the user, and notably to prevent said user from having to grip said candle using the peripheral wall 7 thereof, which may potentially be scorching after the use of said candle.

In particular, the gripping tab 15 may extend horizontally from the top edge 7a of the peripheral wall 7, or vertically between said top edge and a bottom edge 7b of said peripheral wall.

The candle 2 may be used alone, notably arranged on any type of supporting surface, for example a table or any item of furniture. Furthermore, as shown in FIGS. 4 and 5, the candle 2 may be used with a suitable holder 4, notably with a recess 11 wherein at least one pot 1 of said candle is intended to be arranged, so as to form an assembly which may notably be marketed as is.

In the embodiments shown, the holder 4 essentially has an aesthetical function, notably presented in the form of a candle jar. Alternatively, the holder 4 may have further functions, for example having a heating platform extending above the recess 11 for receiving the candle 2 and whereon an element to be heated, for example an essential or scented oil, or a food product, may be arranged by combusting the body 3 of said candle.

In FIGS. 4 and 5a, 5b, the recess 11 has a complementary geometry to that of the pot 1, notably with a view to enhancing the hold of the candle 2 on the holder 4. In particular, the candle 2 is arranged entirely in the recess 11, making it possible to enhance the appearance of the assembly.

Advantageously, the holder 4 may have openings opening into the recess 11 so as to be in communication with the network of elements 9 of the pot 1, so as to enable air circulation between the outside of said recess and the bottom face 6a of the base 6, and thus limit the heating of the pot 1 by thermal convection.

With reference to FIGS. 5a and 5b, the holder 4 has longitudinal tabs 12 which are arranged in a circle at angular intervals according to a constant distance, the recess 11 being formed in said circle, the air circulation between said recess and the exterior of the holder 4 being carried out via angular gaps 13 formed between two adjacent tabs 12.

Furthermore, the angular distance of the gaps 13 may be arranged to allow the passage of a gripping tab 16 borne by the pot 1, so as to enable the user to arrange the candle 2 easily in the recess 11, or remove said candle easily from said recess, merely by gripping said tab 16.

The invention claimed is:

1. A pot comprising:
   a base and a peripheral wall defining a recess together wherein at least one lower portion of a combustible body is configured to be arranged to form a candle, wherein the base comprises a network of elements extending in a relief pattern from the bottom face of said base, said network configured to limit the thermal heating of said pot during the combustion of the body; wherein the network comprises elements angularly equidistributed according to a two-by-two alternation between two types of different geometries.

2. The pot according to claim 1, wherein the network comprises elements which are angularly equidistributed on the bottom face of the base.

3. The pot according to claim 1, wherein the network comprises two types of elements in a relief pattern of different geometries.

4. The pot according to claim 1, wherein the elements are formed by bossing on the base.

5. The pot according to claim 1, wherein the elements of the network are distributed on the base to provide support for the candle.

6. The pot according to claim 1, wherein the peripheral wall comprises a top edge defining a top opening for access to the recess, said pot comprising a lid configured reversible on said top edge to seal said recess by concealing said top opening.

7. The pot according to claim 1, wherein the pot further comprises a gripping tab extending radially from the peripheral wall.

8. A candle comprising a body made of combustible material and a pot according to claim 1, at least one lower portion of said combustible body being arranged in the recess of said pot.

9. The candle according to claim 8, wherein the combustible body is arranged entirely in the recess of the pot.

10. An assembly comprising:
    a candle according to claim 1; and
    a holder for receiving said candle, said holder having a recess wherein at least the pot is intended to be arranged.

11. The assembly according to claim 10, wherein the recess has a complementary geometry to that of the pot.

12. The assembly according to claim 10, wherein the holder has openings opening into the recess so as to be in communication with a network of elements of the pot.

\* \* \* \* \*